United States Patent [19]

Lim et al.

[11] 3,954,966

[45] May 4, 1976

[54] INFUSION SOLUTIONS AND METHOD OF MANUFACTURING SAME

[75] Inventors: Drahoslav Lim, Stanford, Calif.; Ladislav Sprincl, Stodulky-Haje, Czechoslovakia; Jindrich Kopecek, Czechoslovakia; Jiri Vacik, both of Prague, Czechoslovakia

[73] Assignee: Ceskoslovenska akademie ved, Prague, Czechoslovakia

[22] Filed: Mar. 20, 1974

[21] Appl. No.: 453,082

Related U.S. Application Data

[63] Continuation of Ser. No. 228,269, Feb. 22, 1972, abandoned, which is a continuation-in-part of Ser. No. 147,680, May 27, 1971, abandoned.

[30] Foreign Application Priority Data

June 8, 1970  Czechoslovakia ................. 3992-70

[52] U.S. Cl. ............................................. 424/81
[51] Int. Cl.$^2$ ........................................ A61K 31/78
[58] Field of Search ............................. 424/78, 81

[56] References Cited
UNITED STATES PATENTS

| | | |
|---|---|---|
| 2,984,639 | 5/1961 | Stamberger et al. ............ 424/81 X |
| 3,563,925 | 2/1971 | Kliment et al. ..................... 260/8 |
| 3,590,125 | 6/1971 | Hymes .............................. 424/78 |
| 3,701,764 | 12/1972 | Hargitay ........................ 424/80 X |

Primary Examiner—Leonard Schenkman

[57] ABSTRACT

Surgical infusion solutions, useful particularly as blood plasma substitutes, comprising physiological solution of polymers or copolymers formed from ethyleneglycol acrylates and methacrylates, acrylamide, methacrylamide and acrylamides and methacrylamides substituted on the nitrogen atom with either one or two lower alkyl radicals and/or one or two hydroxyalkyl or dihydroxyalkyl radicals containing 1 to 6 carbon atoms and mixtures of these polymeric materials dissolved in a physiological solvent therefor. The polymerization or copolymerization is carried out by solution polymerization methods and the polymeric material is precipitated by mixing it in a suitable nonsolvent therefor, but which is miscible with the polymerization solvent.

13 Claims, No Drawings

INFUSION SOLUTIONS AND METHOD OF MANUFACTURING SAME

This application is a continuation of copending application 228,269, filed Feb. 22, 1972 which in turn was a continuation-in-part of copending application, Ser. No. 147,680, filed May 27, 1971, both entitled INFUSION SOLUTIONS AND METHOD OF MANUFACTURING THE SAME and both now abandoned.

BACKGROUND OF THE INVENTION

Transfusion of blood and blood plasma is now one of the most effective means for treating major hemorrhages resulting from burns and states of shock and other causes. Under extraordinary conditions, such as in wars or major disasters, transfusions are very often carried out with considerable difficulty, particularly in regard to the availability of sufficient quantities of blood or of blood of individual groups. Restricted preservation time, sensitivity to noxious factors, as well as exacting conditions of transport and storage make large stockpiles almost impossible. Further, inconveniences arise from the necessity of blood group determination and cross tests. All of these inconveniences were apparent as early as prior to and during World War I. However, at that time all efforts to find suitable blood plasma substitutes such as those containing gum arabic or gelatin were not successful.

In 1878 it was known that physiological solutions were suitable as substitutes for blood in the treatment of hemorrhages. However, they were of limited use until the fundamental difference between crystalloids and blood and blood plasma were discovered and it was established that the therapeutic effect of these physiological solutions depends mainly on the colloid-osmotic properties thereof. It was also established that for bed patients the most important thing is to replace the lost volume of blood and not the lost erythrocytes. The influence of this knowledge appeared in further work concerning the discovery of better blood plasma substitutes having better colloid-osmotic properties than the then known physiological solutions had. As a result many plasma substitutes were suggested but few proved applicable.

It is therefore, a primary object of the invention to provide new blood plasma substitutes having good colloid-osmotic properties and comprising physiological solutions of polymers or copolymers on monoesters of acrylic and/or methacrylic acid either with aliphatic polyols having at least two hydroxylic groups and one etheric group, or at least three hydroxylic groups, or consisting of N-mono-or di-substituted or non-substituted amides of said acids, the substituents being either lower alkyls with 1-4 carbon atoms, or hydroxyalkyl groups with one or more hydroxylic groups and containing 1-6 carbon atoms and wherein, if desired, the copolymers may contain a minor amount of other monomer units such as ethylene glycol monoethacrylate, methyl methacrylate and the like in an amount which does not affect the water-solubility of the copolymer or wherein various of the monomers may be also mutually copolymerized.

Another object of the invention is a method of manufacturing blood plasma substitutes consisting in carrying out the polymerization or copolymerization in a solution, preferably, in an aqueous solution, although other known polymerization solvents can be used and then precipitating the polymer out of the solution thus obtained by pouring it into an excess of a non-solvent for the polymer or copolymer, the non-solvent being miscible with the primary solvent in which the polymerization or copolymerization takes place and subsequently dissolving the precipitate in a physiological solution.

BROAD STATEMENT OF THE INVENTION

Generally, infusion solutions in accordance with the invention comprise water soluble polymers or copolymers formed from monomers selected from the group consisting of mono-, di- and tri- ethylene glycol esters of methacrylic and acrylic acids, glycerine methacrylate, acrylamide, methacrylamide and N, N-disubstituted methacrylamides and/or acrylamides substituted on the nitrogen atom with one or two radicals selected from the group consisting of lower alkyl radicals containing 1 to 4 carbon atoms, hydroxyalkyl radicals and dihydroxyalkyl radicals containing 1 to 6 carbon atoms and mixtures thereof, the polymers or copolymers being dissolved in a physiological solvent therefor.

Briefly, the infusion solutions, in accordance with the invention, are made by polymerizing or copolymerizing the monomers in a solvent therefor, precipitating the so formed polymer or copolymer in a non-solvent therefor, but which is miscible with the polymerization solvent and subsequently dissolving the precipitate in a physiological solvent therefor. The precipitate is a water soluble polymer which may be formed from the monomers selected from the group consisting of mono-, di and tri- ethylene glycol esters of methacrylic and acrylic acids, glycerine methacrylate,
acrylamide,
methacrylamide,
N, N - disubstituted acrylamides
N - monosubstituted methacrylamides
N, N - disubstituted acrylamides
N - monosubstituted acrylamides the substituents on the nitrogen atom being selected from the group consisting of lower alkyl radicals containing 1 to 4 carbon atoms, hydroxyalkyl and dihydroxyalkyl radicals containing 1 to 6 carbon atoms, and mixtures thereof.

PREFERRED EMBODIMENTS OF THE INVENTION

A wide variety of monomers can be employed in the practice of the present invention. Among suitable monomers which can be employed in the practice of this invention, either as homopolymers or copolymers in various combinations are glycol esters of methacrylic and acrylic acid, such as mono-, di-, and tri- ethylene glycol esters, glycerine methacrylate, N,N-disubstituted methacrylamides, N-monosubstituted methacrylamides, N,N-disubstituted acrylamides and N-monosubstituted acrylamides. It is to be noted, however, that, the N,N-disubstituted methacrylamides are employed in amounts of less than 50% by weight in the original mixture since they do not undergo radical homopolymerization and therefore can be used only to form copolymers. Moreover, since the resulting polymer or copolymer need be water soluble, the substituents on the nitrogen is selected from the group consisting of lower alkyl radicals, lower hydroxyalkyl radicals, lower polyhydroxyalkyl radicals and lower aminoalkyl radicals, generally containing from about 1 to about 6 carbon atoms in the alkyl portion.

Among the most suitable monomers which can be used in carrying out the invention are diethyleneglycol and mono-methacrylate, triglycol monomethacrylate, N-mono-substituted methacrylamides, N-mono- and di- substituted acrylamides having substituents such as those mentioned above and mixtures of these monomers. Additional co-monomers include and which are used in minor amounts (less than 50%) N,N-disubstituted methacrylamides, ethyleneglycol monomethacrylate, N-vinyl pyrrolidone, methyl methacrylate and others provided that the amount is chosen so that solubility and of the copolymers in water and physiological solutions is preserved. The glycol methacrylates acrylates may also contain small amounts of the respective diester, provided that the polymerization is carried out in solutions which are so dilute that cross-linking cannot take place.

Polymerization can be carried out with any of the known compounds or redox systems which liberate active free radicals in accordance with known procedures. The solvents used in the polymerization may be water, ethanol, dimethylformamide and the like and other well-known polymerization solvents. Upon completion of polymerization, the polymeric product can be precipitated by a wide variety of known non-solvent agents which are miscible with the polymeric solvent such as diethylether, acetone or mixtures thereof and similar agents and repeatedly fractionated with such agents by known procedures to obtain a fraction of suitable average molecular weight which can be determined, e.g., by light scattering.

The polymeric or copolymeric product can vary widely in regard to useful average molecular weight and the product can be dissolved in physiological solutions to provide solutions which exhibit a widely varying viscosity. Generally, however, successful use is dependent on molecular weight and an optimal average molecular weight, although not critical, is lower than 150,000. The product exhibits a relatively narrow molecular weight distribution in a given fraction. In general, the higher average molecular weight materials stay in the blood for a longer period of time. Moreover, although the amount of polymeric product dissolved in physiological solution is not critical and may vary widely, generally in solutions, the product has a viscosity of from about 1 to 3 centipoises. It is to be noted, however, that solutions of viscosities of less than 1 centipoise and greater than 3 centipoises can be employed.

Generally, the physiological solvent is an aqueous sodium chloride solution, although other solutions of similar composition can be used and the concentration of polymeric product in the solution is not critical, the amount being used of a polymer of a given molecular weight sufficient to form a solution of desired and useful viscosity.

Polymeric substances of the invention are non-toxic, provoking no allergy or similar reactions. They are not antigenic, do not distort the blood group determination and are very stable.

All types of the above stated infusion solutions were tested with good results by treating hemorrhagic shocks of rabbits.

For instance, the polymer of triethylene monomethacrylate was used for sensitization of five rabbits of the same sex and the same average weight of 2.5 kg, in five subcutaneous injections of 2 ml each in 4 day intervals. The evaluation of the tests was carried out by biological and serological methods 30 days after the last sensitizing injection. As a control for the biological tests, non-sensitized rabbits were used. The serological methods were carried out by means of rabbit serum and physiological solution. The following results were obtained:

A. BIOLOGICAL TESTS

Arthus reaction was provoked by intracutaneous injections of 1 ml of the solution. Histological examination of the injection sites showed after 4 to 48 hours no difference in comparison with the control group and the reaction was evaluated as negative.

Anaphalaxis reaction was also provoked after 30 days from the last sensitizing injection by injection of 20–50 ml of the solution into the heart. No reaction could be observed.

B. SEROLOGICAL METHODS

Agglutination test: One drop of the infusion solution was mixed with one drop of the serum of the sensibilized test rabbits. For the control, normal serum and physiological solutions were used. The results were observed after 5, 10, 15 and 20 minutes under a microscope. In no case was an agglutination established.

Agglutination in test tubes: Into 12 ml conical test tubes 0.5, 1.0, 2.0, 3.0 and 4.0 ml of the serum were added together with 3 ml of the infusion solution. The control was carried out using normal serum and physiological solution. In none of the test tubes was agglutination observed.

Double diffusion in two directions (Ouchterlony's method) was also determined as follows: The test solution was placed in a Petri dish having a central reservoir (16 mm diameter) and filled with agar. Other Petri dishes having reservoirs (12 mm diameter) were filled with the serum of sensibilized rabbits to a distance of 10 mm from the central reservoir. The dishes were kept in a refrigerator for 4 weeks. No diffusion of anti-matter was noted.

Thus, the above methods of anaphloxy did not prove any formation of anti-matter.

In order to illustrate the present invention more fully, the following illustrative examples are given. It is to be understood that the examples are not limitative.

EXAMPLE 1

The example illustrates the polymerization procedure.

A mixture of 14 grams of N- (2-hydroxypropyl methacrylamide), 38 grams of methanol, 155 grams of water and 0.58 grams of methyl azobisisobutyrate were weighed into a glass ampoule under a nitrogen blanket for one hour to remove the dissolved oxygen, sealed and polymerized at 60°C for 3 hours. The mixture was then cooled and precipitated into a 10-fold excess of 1:1 mixture of acetone and diethylether as a precipitating agent. 10.6 grams of the polymer thus obtained was dissolved in 250 ml of methanol and fractionated at 20°C by slow dropwise addition of the precipitating agent. After the first turbidity had appeared the mixture was left to stand overnight. The precipitated fraction of the polymer was filtered by suction and the precipitation was again carried out by slow dropwise addition of precipitating agent until seven fractions were obtained. Each fraction was reprecipitated by dissolving in methanol precipitating into the 1:1 acetone and diethylether mixture. The molecular weight of the individual fractions was determined by light scattering and the average molecular weight of the individual fractions was in a range of 10,000–350,000. Each fraction was dissolved in an aqueous sodium chloride solution to form synthetic infusion solutions of 2 centipoises viscosity.

EXAMPLE 2

10 g Of triethyleneglycol monomethacrylate, 90 g of water and 0.009 g of iso-bis-methylisobutyrate were weighed into a glass ampoule under a stream of nitrogen which was passed for 1 hour through the solution. The ampoule was sealed and heated 10 hours to 60°C. The cooled solution was precipitated into 10-fold volume of acetone. The precipitate was sucked off, washed with acetone and dried. The polymer was then dissolved in water and divided into three fractions using a system of acetone-water. The middle fraction was used for preparing a blood plasma substitute by dissolving the washed and vacuum-dried polymer in physiological solution at a 0.5% concentration having a viscosity of 2.3 centipoises. The solution was kept in a refrigerator and sterilized before use by 20 minutes boiling.

EXAMPLE 3

20 g Of N-ethyl methacrylamide, 80 g of water and 0.02 g of diisopropyl percarbonate were weighed into a glass ampoule, flushed with nitrogen for 1 hour, sealed and polymerized 10 hours at 60°C. The cooled solution was precipitated into acetone, the precipitate sucked off, washed and dried. The polymer, from which all remaining solvent was removed was then dissolved in sodium chloride physiological solution. The concentration of the solution was chosen so that the viscosity equaled that of qenuine blood plasma.

EXAMPLE 4

20 g Of a mixture of N-ethyl-methacrylamide and N-N-di-methyl methacrylamide (molar ratio 5 : 1), 80 of water and 0.02 g of di-isopropyl percarbonate where weighed into a glass ampoule, flushed 1 hour with nitrogen, the ampoule sealed and the solution copolymerized 10 hours at 70°C. The solution was then treated as described in EXAMPLE 3.

EXAMPLE 5

15 g Of N,N-dimethyl acrylamide, 84 g of water and 1 g of a 30% aqueous hydrogen peroxide solution were polymerized in a glass ampoule 10 hours at 70°C in the way described in foregoing EXAMPLES and an infusion solution formed as in the foregoing EXAMPLES.

EXAMPLE 6

20 g Of a mixture of triethyleneglycol monomethacrylate and N-vinyl pyrrolidone (molar ratio 4 : 1), 40 g of ethyl alcohol, 40 g of water and 0.01 g of azo-bis-isobutyronitrile was polymerized 10 hours at 60°C and processed in the manner described in EXAMPLES 2 and 3.

EXAMPLE 7

30 g Of glycerol monoethacrylate, 70 g of water and 0.01 g of di-isopropyl percarbonate were polymerized 10 hours at 60°C. The solution was processed in the manner described in EXAMPLE 3.

EXAMPLE 8

20 g Of a mixture of glycerol monomethacrylate and methyl methacrylate (molar ratio 7-1), 80 g of water and 0.01 g of azo-bis-isobutyronitrile were polymerized 10 hours at 60°C. Further treatment was carried out as in EXAMPLE 2.

All of the solutions proposed in accordance with the EXAMPLES, as well as the others described above in more general terms are useful as infusion solutions in cases where blood loss has occurred such as from injuries, bleeding, anti-shock treatment, radiation disease treatment, burns and in cases of large losses of blood liquids. In addition, they are useful where external blood circulation is carried out such as in the use of an artificial heart.

Numerous other uses and advantages of the solutions of this invention will be readily apparent to those skilled in the art.

Accordingly, it is to be understood that many variations of the disclosed embodiments of this invention may be made without departing from the spirit and scope thereof and this invention is not to be limited except as defined in the appended claims.

What is claimed is:

1. A method for extending blood in a subject requiring such treatment which comprises infusing into said subject, in an amount necessary to replace lost blood, a solution having a viscosity of about 1 to 3 centipoise of a physiologically acceptable aqueous solvent and water soluble polymer formed from monomers selected from the group consisting of mono-, di-, or tri- ethylene glycol esters of methacrylic and acrylic acid,
   glycerine methacrylate,
   acrylamide,
   methacrylamide,
   N, N - disubstituted methacrylamides,
   N - monosubstituted methacrylamides,
   N, N - disubstituted acrylamides,
   N - monosubstituted acrylamides and mixtures thereof,
the substituents on the nitrogen atom being selected from the group consisting of
   lower alkyl radicals containing 1 to 4 carbon atoms,
      hydroxyalkyl and dihydroxyalkyl radicals containing 1 to 6 carbon atoms.

2. The method of claim 1 wherein said monomers are selected from the group consisting of triethylene glycol methacrylate, glycerine methacrylate, N-mono-substituted acrylamide, N,N-di-substituted acrylamide and N-mono-substituted methacrylamide.

3. The method of claim 1 wherein said monomers are selected from the group consisting of triethylene glycol methacrylate, glycerine methacrylate, N-ethylmethacrylamide, N,N-dimethylacrylamide and N-(2-hydroxypropylmethacrylamide).

4. The method of claim 1 wherein said monomers are selected from the group consisting of N-ethyl-methacrylamide, N,N-dimethylacrylamide and N-(2-hydroxypropylmethacrylamide).

5. A method of manufacturing a solution for use in extending blood which comprises the steps of polymerizing a monomer under free radical conditions in a solvent for both said monomer and the polymer thereby formed, said monomer being selected from the group consisting of mono-, di-, or tri- ethylene glycol esters of methacrylic and acrylic acid,
   glycerine methacrylate, acrylamide,
methacrylamide,
N, N - disubstituted methacrylamides,
N - monosubstituted methacrylamides,
N, N - disubstituted acrylamides,
N - monosubstituted acrylamides, and mixtures thereof, the substituents on the nitrogen atom being selected from the group consisting of
   lower alkyl radicals containing 1 to 4 carbon atoms,
   hydroxyalkyl and dihydroxyalkyl radicals containing 1 to 6 carbon atoms,
until a polymer is formed having a molecular weight below 150,000, precipitating the thusly formed polymer by addition of a precipitating agent for said polymer which is a non-solvent for said polymer and which is miscible with the solvent in which the polymerization had been carried out and thereafter dissolving the thus precipitated polymer in a physiologically acceptable solvent therefor in an amount sufficient to provide a solution having a viscosity of about 1 to 3 centipoise.

6. A method as defined in claim 5 wherein said monomer is N-(2-hydroxypropylmethacrylamide), said solvent is methanol, said non-solvent is a mixture of acetone and diethylether and said physiologically acceptable solvent in aqueous sodium chloride.

7. A method as defined in claim 5 wherein said monomer is triethylene glycol monomethacrylate, said solvent is water, said non-solvent is acetone and said physiologically acceptable solvent is aqueous sodium chloride.

8. A method as defined in claim 5 wherein said monomers are N-ethylacrylamide and N,N-dimethylacrylamide, said solvent is water, said non-solvent is acetone and said physiologically acceptable solution is aqueous sodium chloride.

9. A method as defined in claim 5 wherein said monomer is glycerol monoethacrylate, said solvent is water, said non-solvent is acetone and said physiologically acceptable solution is aqueous sodium chloride.

10. A method as defined in claim 5 wherein said monomers are glycerol monomethyacrylate and methylmethacrylate, said solvent is water, said non-solvent is acetone and said physiologically acceptable solvent is aqueous sodium chloride.

11. A method as defined in claim 5 wherein said precipitating agent is selected from the group consisting of acetone, diethylether, and mixtures thereof.

12. A method as defined in claim 5, wherein said physiological solvent is a solution of sodium chloride dissolved in distilled water, wherein the concentration of sodium chloride is less than 1.0%.

13. A method as defined in claim 5, wherein said free radical polymerization is effected at a temperature of at least 60°C in an inert atmosphere for a period of time sufficient to effect polymerization.

* * * * *